United States Patent [19]
Lai et al.

[11] Patent Number: 5,344,765
[45] Date of Patent: Sep. 6, 1994

[54] DNA ENCODING POLYPEPTIDES WITH ACTIVITY AGAINST GRAM-POSITIVE AND GRAM-NEGATIVE BACTERIA

[75] Inventors: Jiunu S. Lai; Jar-How Lee, both of Los Angeles; James E. Callaway, Orinda, all of Calif.

[73] Assignee: Xoma Corporation, Berkeley, Calif.

[21] Appl. No.: 10,676

[22] Filed: Jan. 28, 1993

Related U.S. Application Data

[60] Continuation-in-part of Ser. No. 637,199, Jan. 3, 1991, Pat. No. 5,206,154, which is a division of Ser. No. 474,304, Feb. 5, 1990, Pat. No. 5,028,530, which is a continuation of Ser. No. 797,472, Nov. 13, 1985, abandoned, which is a continuation-in-part of Ser. No. 695,309, Jan. 28, 1985, abandoned.

[51] Int. Cl.$^5$ .................... C07K 7/00; C12N 15/62
[52] U.S. Cl. .................. 435/69.7; 435/320.1; 530/370; 530/350; 536/23.4
[58] Field of Search ............. 435/69.7, 172.3, 320.1; 530/350, 300, 320; 536/23.4

[56] References Cited

U.S. PATENT DOCUMENTS

| | | | |
|---|---|---|---|
| 4,332,892 | 6/1982 | Ptashne et al. | 435/68 |
| 4,335,104 | 10/1982 | Hultmark et al. | 435/70 |
| 4,366,246 | 12/1982 | Riggs | 325/68 |
| 4,499,188 | 2/1985 | Konrad et al. | 435/70 |
| 4,520,016 | 5/1985 | Hultmark et al. | 514/12 |
| 5,028,530 | 7/1991 | Lai et al. | 435/69.1 |
| 5,166,321 | 11/1992 | Lai et al. | 530/324 |

FOREIGN PATENT DOCUMENTS

| | | |
|---|---|---|
| 8403103 | 8/1984 | PCT Int'l Appl. |
| WO85/01746 | 4/1985 | PCT Int'l Appl. |
| WO86/04356 | 7/1986 | PCT Int'l Appl. |
| 2084584 | 10/1990 | United Kingdom |

OTHER PUBLICATIONS

Andreu, D. et al., "N-terminal analogues of cecropin A: synthesis, antibacterial activity, and conformational properties", *Biochemistry* 24:1683-1688 (1985).

Andreu, D. et al., "Solid-phase synthesis of cecropin A and related peptides", *Proc. Natl. Acad. Sci. USA* 80:6475-6479 (Nov. 1983).

Andreu, D. et al., "Synthetic analogs of cecropin A", *Chemical Abstracts* 103:769, Abstract No. 123890t (1985).

Boman, H. G. and Steiner, H., "Humoral Immunity in cecropia pupae", *Current Topics Microbiol. Immun.* 94/95:75-91 (1981), Spring-Verlag Publishers.

Casadaban, M. J., "Fusion of the *Escherichia coli lac* genes to the ara promoter: a general technique using bacteriophage Mu-1 insertions", *Proc. Natl. Acad. Sci. USA* 72(3):809-813 (Mar. 1975).

Clarke et al., "The nucleotide sequence of the araC regulatory gene in *Salmonella typhimurium* LT2", *Gene* 18:157-163 (1982).

DeGrado, W. F., "Solution phase synthesis of cecropin A 1-22 and potent analogs thereof using segments prepared on an oxime solid phase support", *Chemical Abstracts* 101:742, Abstract No. 171691j (1984).

Gibbs et al., "Intrinsic GTPase activity distinguishes normal and oncogenic ras p21 molecules", *Proc. Natl. Acad. Sci. USA* 81:5704-5708 (Sep. 1984).

Greenfield et al., "DNA sequence of the araBAD promoter in *Escherichia coli* B/r", *Proc. Natl. Acad. Sci. USA* 75(10):4724-4728 (Oct. 1978).

Hedge, P. J. and Spratt, B. G., "A gene fusion that localises the penicillin-binding domain of penicillin-binding protein 3 of *Escherichia coli*", *FEBS Lett.* 176(1):179-184 (Oct. 1984).

(List continued on next page.)

*Primary Examiner*—Robert J. Hill, Jr.
*Assistant Examiner*—John D. Ulm
*Attorney, Agent, or Firm*—Sterne, Kessler, Goldstein & Fox

[57] ABSTRACT

The invention relates to cecropin-like polypeptides with a variety of C-terminus modifications. Conversion of the terminal carboxy group to a homoserine extended neutral, negatively charged or positively charged form results in the polypeptides of the invention that have significant bactericidal effects against both Gram-positive and Gram-negative bacteria.

9 Claims, 4 Drawing Sheets

OTHER PUBLICATIONS

Heusterspreute et al., "Expression of galactokinase as a fusion protein in *Escherichia coli* and *Saccharomyces cerevisiae*", *DNA* 3(5):377–386 (1984).

Horwitz et al., "Construction of pBR 322–ara hybrid plasmids by in vivo recombination", *Molec. Gen. Genet.* 179:615–625 (1980).

Horwitz et al., "DNA sequence of the *araBAD–araC* controlling region in *Salmonella typhimurium* LT2", *Gene* 14:309–319 (1981).

Hultmark et al., "Insect immunity: isolation and structure of cecropin D and four minor antibacterial components from cecropia pupae", *Eur. J. Biochem.* 127:207–217 (1982).

Hurt et al., "The amino-terminal region of an imported mitochondrial precursor polypeptide can direct cytoplasmic dihydrofolate reductase into the mitochondrial matrix", *EMBO J.* 3(13):3149–3156 (1984).

Johnston et al., "High–level expression of M13 gene II protein from an inducible polycistronic messenger RNA", *Gene 34:137–145 (1985)*.

Kaplan et al., "Hybrid plasmids containing the araBAD genes of *Escherichia coli* B/r", *Gene* 3:177–189 (1978).

Kempe et al., "Multiple-copy genes: production and modification of monomeric peptides from large multimeric fusion proteins", *Gene* 39:239–245 (1985).

Kempe et al., "Production and characterization of growth hormone releasing factor analogs through recombinant DNA and chemical techniques", *BioTechnology* 4:565–568 (Jun. 1986).

Kuhn, A. and Wickner, W., "Isolation of mutants in M13 coat protein that affect its synthesis, processing, and assembly into phage", *J. Biol. Chem.* 260(29):15907–15913 (Dec. 15, 1985).

Lee et al., "Isolation of ara–lac gene fusions in *Salmonella typhimurium* LT2 by using transducing bacteriophage Mu d(AP$^r$ lac", *J. Bacteriol.* 143(3):1325–1331 (Sep. 1980).

Lewin, B., Chapter 8–Operon control circuits, *Gene Expression-1*, pp. 323–328, John Wiley & Sons (1982).

Lin et al., "The araBAD operon of *Salmonella typhimurium* LT2", *Gene* 34:111–122 (1985).

Merrifield et al., "Synthesis of the antibacterial peptide cecropin A(1–33)", *Biochemistry* 21:5020–5031 (1982).

Miyada et al., "Five mutations in the promoter region of araBAD operon of *Escherichia coli* B/r", *J. Bact.* 156(2):765–772 (Nov. 1983).

Qu et al., "Insect immunity: isolation and structure of cecropins B and D from pupae of the Chinese oak silk moth, *Antheraea pernyi*", *Eur. J. Biochem.* 127:219–224 (1982).

Reiss et al., "Protein fusions with the kanamycin resistance gene from transposon Tn5", *EMBO J.* 3(10):3317–3322 (1984).

Rüther, U. and Müller-Hill, B., "Easy identification of cDNA clones", *EMBO J.* 2(10):1791–1794 (1983).

Schleif, R. and Greenblatt, J., "Dual control of arabinose genes on transducing phage λdara", *J. Mol. Biol.* 59:127–150 (1971).

Schleif, R. and Greenblatt, J., "Transcription in the lambda-ara phage", *Cold Spring Harbor Symp. Quant. Biol.* 35:369–373 (1970).

Steiner et al., "Sequence and specificity of two antibacterial proteins involved in insect immunity", *Nature* 292:246–248 (Jul. 16, 1981).

Steiner, H., "Secondary structure of the cecropins: antibacterial peptides from the moth *Hyalophora cecropia*", *FEBS Lett.* 137(2):283–287 (Jan. 1982).

van Hofsten, P. et al., "Molecular cloning, cDNA sequencing, and chemical synthesis of cecropin B from *Hyalophora cecropia*", *Proc. Natl. Acad. Sci. USA* 82:2240–2243 (Apr. 1985).

van Hofsten, P. et al., "Molecular cloning, cDNA sequencing, and chemical snythesis of cecropin B from *Hyalophora cecropia*", *Chemical Abstracts* 103:127–128, Abstract No. 48969v (1985).

Wilcox et al., "Chapter 12–DNA sequence analysis of mutants in the araBAD and araC promoters", *Promoters: Structure and Function*, pp. 183–194, Rodriguez and Chamberlin, Eds., Prager (1982).

SCHEME OF CECROPIN MODIFICATION

Ara-B----Met-CA-met-gly

CNBr digestion ↓

TFA ↓

CA-homoserine lactone

NH₄OH ↙ ↘ Ethylenediamine

CA-homoserineamide     CA-homoserine-NH-Et-NH₂

DNA ENCODING POLYPEPTIDES WITH ACTIVITY AGAINST GRAM-POSITIVE AND GRAM-NEGATIVE BACTERIA

CROSS REFERENCE TO RELATED APPLICATION

This application is a continuation-in-part of application Ser. No. 07/637,199, filed Jan. 3, 1991, (now U.S. Pat. No. 5,206,154) which is a divisional of application Ser. No. 07/474,304, filed Feb. 5, 1990 (now U.S. Pat. No. 5,028,530, issued Jul. 2, 1992), which is a continuation of application Ser. No. 06/797,472, filed on Nov. 13, 1985, (abandoned), which is a continuation-in-part of application Ser. No. 06/695,309, filed Jan. 28, 1985 (abandoned), all of which are incorporated herein by reference.

BACKGROUND OF THE INVENTION

1. Field of the Invention

The present invention relates to polypeptides and more specifically to cecropin-like polypeptides with various C-terminus modifications. These modified Cecropin-like polypeptides exhibit increased potency and broader spectrum of antimicrobial activity than the cecropins. This invention also relates to methods of producing these modified cecropins and methods of suppressing the growth of Gram-negative or Gram-positive bacteria by their administration.

2. Brief Description of the Background Art

The immune system of the *Cecropia* moth and several lepidopteran insects is characterized by an effective humoral response which is mainly associated with the cecropins, a recently discovered family of antibacterial peptides (Boman, H. G. and Steiner, H., Current Topics In Microbiology and Immunology 94/95:75–91 (1981). Three major cecropins, A, B, and D, have been purified from immune hemolymph and their sequences have been elucidated (Qu et al., European Journal of Biochemistry 127:219–224 (1982); Hultmark et al., Ibid, 127:207–217 (1982); and Hultmark et al., U.S. Pat. Nos. 4,355,104 and 4,520,016). All cecropins are small basic peptides with a high degree of mutual sequence homology. The amino acid sequences of cecropins A, B and D from *Antheraea pernyi* (A.p.) and from *Hylophora cecropia* (H.c.) are as follows:

|  | 1 | 5 | 10 |
|---|---|---|---|
| A.p. Cecropin B | H₂N—Lys—Trp—Lys—Ile— | Phe—Lys—Lys—Ile—Glu— | Lys—Val—Gly—Arg— |
| H.c. Cecropin B | H₂N—Lys—Trp—Lys—Val— | Phe—Lys—Lys—Ile—Glu— | Lys—Met—Gly—Arg— |
| H.c. Cecropin A | H₂N—Lys—Trp—Lys—Leu— | Phe—Lys—Lys—Ile—Glu— | Lys—Val—Gly—Gln— |
| H.c. Cecropin D | H₂N—Trp—Asn—Pro—Phe— | Lys—Glu—Leu—Glu— | Lys—Val—Gly—Gln— |
| A.p. Cecropin D | H₂N—Trp—Asn—Pro—Phe— | Lys—Glu—Leu—Glu— | Arg—Ala—Gly—Gln— |

|  | 15 | 20 | 25 |
|---|---|---|---|
| A.p. Cecropin B | Asn— Ile —Arg—Asn—Gly— | Ile— Ile —Lys—Ala—Gly— | Pro—Ala—Val—Ala— |
| H.c. Cecropin B | Asn— Ile —Arg—Asn—Gly— | Ile—Val—Lys—Ala—Gly— | Pro—Ala—Ile—Ala— |
| H.c. Cecropin A | Asn— Ile —Arg—Asp—Gly— | Ile— Ile —Lys—Ala—Gly— | Pro—Ala—Val—Ala— |
| H.c. Cecropin D | Arg—Val—Arg—Asp—Ala— | Val—Ile—Ser—Ala—Gly— | Pro—Ala—Val—Ala— |
| A.p. Cecropin D | Arg—Val—Arg—Asp—Ala— | Ile —Ile —Ser—Ala—Gly— | Pro—Ala—Val—Ala— |

|  | 30 | 35 |
|---|---|---|
| A.p. Cecropin B | Val—Leu—Gly—Glu—Ala— | Unknown C-terminal |
| H.c. Cecropin B | Val—Leu—Gly—Glu—Ala— | Lys— Ala —Leu—CO—R |
| H.c. Cecropin A | Val—Val—Gly—Gln—Ala— | Thr—Gln— Ile —Ala—Lys—CO—R |
| H.c. Cecropin D | Thr—Val—Ala —Gln—Ala— | Thr—Ala —Leu—Ala—Lys—CO—R |
| H.c. Cecropin D | Thr—Val—Ala —Gln—Ala— | Thr—Ala —Leu—Ala—Lys—CO—R |

The natural cecropins possess antibacterial activity against a variety of bacteria including both Gram-negative and Gram-positive bacteria. The available data on the mode of action of the cecropins indicate that they disrupt the cytoplasmic membranes of bacteria (Steiner et al., Nature 292:246–248 (1981)). It is apparent from the literature that different bacterial species have different sensitivities to the cecropins, and that each cecropin has a distinct spectrum of activity. For example, *Bacillus megaterium* is highly sensitive to cecropins A and B, but relatively resistant to cecropin D. Both Gram-negative and Gram-positive organisms have been shown to be sensitive to cecropins in the micromolar concentration range. Organisms showing a high level of sensitivity to cecropins include *Escherichia coli, Pseudomonas aeruginosa, Bacillus megaterium,* and *Salmonella typhimurium*.

Although cecropins A and B have eight amino acid replacements within the first 32 residues and possess unique C-terminal sequences, their activities against nine different bacterial species are very similar. This suggests that many amino acid substitutions can be tolerated without altering the biological activity of the peptide. Similarly, cecropin B from the Chinese oak silk moth (*A. pernyi*) differs from cecropin B from North American silk moths (*H. cecropia*) at four positions; however, three of the changes are replacements for the corresponding amino acids found in the *H. cecropia* A form. The fourth change is in a position where *H. cecropia* A and B forms differ and is a conservative change.

The carboxyl terminus in all naturally occurring cecropins is blocked and, in the case of cecropin A, the blocking group R is a primary amide (Andreu et al., P.N.A.S. USA 80:6475-6479 (1983)). Cecropin A and several related peptides have recently been synthesized by solid phase techniques and have been shown to be totally indistinguishable from natural cecropin A by chemical and physical criteria as well as biological activity when the C-terminus was amidated (Andreu et al., supra). We have observed that the modification of the carboxy terminus is required for bactericidal activity in the micromolar concentration range against most Gram-positive and some Gram-negative bacteria.

The covalent modification of the carboxy terminus of proteins can be achieved quantitatively by the cleavage at methionyl residues with cyanogen bromide. This chemical cleavage results in the formation of C-terminal homoserine lactone which can be modified by a variety of chemical agents (Horn, Analytical Biochemistry 69:583-589 (1975); Kempe et al., Gene 39:239-245 (1985); Kempe et at., Biotechnology 4:565-568 (1986)).

In view of the great usefulness of the cecropins and analogs thereof and of the great promise that recombinant DNA methods offer for the production of proteins, it appeared desirable to provide a system for the production of cecropin-like polypeptides by means of such technology. Furthermore, it would be desirable to produce recombinant cecropin-like polypeptides that possess bactericidal activity against both Gram-negative and Gram-positive bacteria as do naturally occurring cecropins.

SUMMARY OF THE INVENTION

The invention relates to cecropin-like polypeptides with a variety of C-terminus modifications. Conversion of the terminal carboxy group to a homoserine extended neutral, negatively charged or positively charged modified forms result in the polypeptides of the invention that have significant bactericidal effects against both Gram-positive and Gram-negative bacteria. Production of cecropin A-like polypeptides is achieved through the expression of the cecropin A-like polypeptide as a fusion protein in $E.\ coli$. This results in the sequestering of the material in inclusion bodies within the bacteria and is not toxic to the host.

The invention also relates to a cecropin-like polypeptide which is extended at the C-terminus thereof by Met-X, wherein X is a group which is cleavable from methionine.

The invention also relates to a DNA molecule comprising a genetic sequence coding for a cecropin-like polypeptide which is extended at the C-terminus by Met-X, wherein X is a group which is cleavable from methionine.

Cecropin A plasmids were constructed to code for elongated cecropin A-like polypeptides with additional C-terminal residues of Met-X, where X is an amino acid or peptide residue, and a methionine at the N-terminal side of the N-terminal amino acid of cecropin. The cecropin A-like polypeptide can be excised by cyanogen bromide digestion to produce cecropin A with a C-terminal homoserine. This can be chemically modified to produce a polypeptide with a broader range of bactericidal activity than natural cecropin A. In addition, the carboxy terminus can be modified by a variety of reagents to target specific classes of bacteria (e.g. CA-HS-COOH for Gram-negative and CA-HS-NH-Et-NH$_2$ for broad range activity).

Of the variety of naturally occurring cecropins listed above, cecropin A is the most preferred. The following sequence of cecropin A was used to produce the cecropin-like polypeptides of the invention:

$$\underset{1}{\text{H2N}}-\text{Lys}-\text{Trp}-\text{Lys}-\text{Leu}-\underset{5}{\text{Phe}}-\text{Lys}-\text{Lys}-\text{Ile}-$$

$$\underset{10}{\text{Glu}}-\text{Lys}-\text{Val}-\text{Gly}-\text{Gln}-\underset{15}{\text{Asn}}-\text{Ile}-\text{Arg}-\text{Asp}-$$

$$\underset{20}{\text{Gly}}-\text{Ile}-\text{Ile}-\text{Lys}-\text{Ala}-\underset{25}{\text{Gly}}-\text{Pro}-\text{Ala}-\text{Val}-$$

$$\text{Ala}-\text{Val}-\text{Val}-\underset{30}{\text{Gly}}-\text{Gln}-\text{Ala}-\text{Thr}-\underset{35}{\text{Gln}}-\text{Ile}-$$

$$\text{Ala}-\text{Lys}-\text{CO}-\text{R1}.$$

The invention also relates to a method of producing a cecropin-like polypeptide which is extended by a homoserine residue at the C-terminus thereof which comprises:

transforming a suitable host with an expression vehicle of this invention;
culturing the host;
recovering said cecropin-like polypeptide, having Met-X at the C-terminus thereof; and
cleaving said Met-X to thereby produce a C-terminal homoserine.

The invention also relates to modified cecropin-like polypeptides, where the naturally occurring CO-R terminus is replaced by an HS-COR$^1$, where HS represents a homoserine residue and COR$^1$ represents COOH, CONH$_2$, a lower alkyl (C$_1$-C$_6$) amide, a lower alkyl ester, or an amide of a C$_2$-C$_4$ alkylenediamine. COR$^1$ also represents a lactone formed together with the hydroxy group of the homoserine residue.

The invention also relates to a pharmaceutical composition with antimicrobial activity against both Gram-negative and Gram-positive bacteria, comprising an effective amount of tile cecropin-like polypeptides or the pharmaceutically acceptable salt thereof, and a pharmaceutically inert carrier.

The invention further relates to a method of suppressing the growth of Gram-positive or Gram-negative bacteria, comprising administering an effective amount of the pharmaceutical compositions of this invention to a composition or patient infected by bacteria.

A significant advancement of this invention over the prior art is the large scale production of cecropin A-like polypeptides made possible by genetic engineering techniques. The preparation of the same amount of material as obtained in a single 10-liter fermentation using the methods of this invention, using the methods disclosed in prior art, would require the use of over two thousand *Cecropia* pupae, each of which requiring extensive handling.

Another advancement is the adaptation of methods to effect C-terminal modification which are feasible for large scale production of a variety of C-terminal adducts. A further advancement is the preparation of carboxyl terminus modified cecropins which exhibit enhanced bactericidal activity compared to the naturally occurring cecropins.

DETAILED DESCRIPTION OF THE INVENTION

The terms cecropin and cecropin-like, as used throughout the specification and claims, are meant to include polypeptides that are the same or related to cecropins isolated from any insect species, which have bactericidal activity in an in vivo or in vitro system acceptable by the art to measure such activity.

These terms are also used in this invention to include any analog, homolog, mutant, isomer or derivative of naturally occurring cecropin, which shows bactericidal activity in an appropriate system. When a cecropin-like polypeptide is said to be homologous to a certain naturally occurring cecropin, the polypeptide possesses a homology of at least 85 percent, preferably at least 90 percent, to the naturally occurring cecropin.

The terms are also meant to include fragments having less than the naturally-occurring number of amino acids, such as partial fragments of natural cecropins, or their analogs. The terms are also meant to include any product which comprises the sequence of a naturally-occurring cecropin or analog thereof, together with one or more flanking amino acids, which show cecropin-like bactericidal activity. These terms are also meant to include polypeptides having less than the number of amino acids in naturally occurring cecropins but which still possess bactericidal activity.

Further, these terms are also meant to include elongated cecropin A-like polypeptides with additional C-terminal residues comprising Met-X, wherein X is an amino acid, an analog of an amino acid, or a peptide which may optionally comprise amino acid analogs.

1. Modified Cecropin-Like Polypeptides

Intermediate products of the invention are modified cecropins with additional Met-X residues. X is a group which may be cleaved from methionine with cyanogen bromide to generate homoserine-elongated cecropin-like polypeptides. X may be an amino acid, an analog of an amino acid, a peptide, or a peptide comprising amino acid analogs. Said amino acids may comprise any of the natural amino acids (See Lehniger, A. L., Biochemistry, Worth Publishers, Inc. (1970), p. 67) or analogs thereof. These elongated cecropin-like polypeptides are digested by cyanogen bromide, which generates homoserine-elongated cecropin-like polypeptides. These elongated cecropin-like polypeptides with a homoserine residue at the C-terminus are then modified to produce a C-terminus that is neutral, negatively charged or positively charged. In tile most preferred embodiment, the homoserine residue is converted to a homoserine derivative at the C-terminus. Neutral derivatives include homoserine lactone and homoserine amide. A positively charged homoserine derivative is the salt of the homoserine amide of $C_2$–$C_4$ alkylenediamine obtained by treatment with a pharmaceutically acceptable acid. A negatively charged homoserine derivative is the salt of the homoserine residue carboxyl group obtained by treatment with a pharmaceutically acceptable base. By the term "pharmaceutically acceptable salt" is intended pharmaceutically acceptable acids or bases which include, but are not limited to, bases such as alkaline earth metal hydroxides, ammonium hydroxides, and alkylammonium hydroxides, or acids such as sulphuric, hydrochloric, hydrobromic, phosphoric, acetic, etc.

The homoserine lactone can be readily formed by cyclization of the homoserine to the lactone form in concentrated trifluoroacetic acid. The formation of the homoserine amide is achieved by the treatment of the lactone form with ammonium hydroxide. The preferred form of the homoserine amide of alkylenediamine is the homoserine amide of ethylenediamine. The ethylenediamine form is derived from the homoserine lactone by addition of ethylenediamine in dimethylsulfoxide.

The preferred cecropin-like polypeptide is produced from the sequence of cecropin A. Other cecropin sequences, such as B or D, can also be used. Consensus sequences obtained by combining some portion of one cecropin with a portion of another different cecropin can also be used.

2. Microbial Production of Cecropin-like Polypeptides

The present invention provides methods of microbiological production of cecropins elongated with additional amino acid residues at the C-terminus, using cecropin-sensitive or resistant hosts. One embodiment of the invention is to express a gene sequence coding for an elongated cecropin-like polypeptide consisting of the group Met-X which lacks bactericidal activity. Thus, the additional amino acid or amino acids of group X may then be subsequently cleaved to yield a protein with bacterial activity.

In another embodiment, the genetic sequence coding for the cecropin-like polypeptide is linked to an inducible promoter, and the resulting genetic construct is introduced into an expression vehicle. The expression vehicle is then utilized to transform an appropriate host and the host is fermented under normal conditions wherein the promoter is not active. After an appropriate period of time, such as, for example, at a time when the cells are in stationary phase, the promoter is induced as by varying an outside environmental factor such as salt concentration, light, presence or absence of a metabolite, a metal, and the like, this change leading to transcription of the cecropin genetic sequence into mRNA, and then translation thereof into the elongated cecropin. Even though the resulting cecropin is bactericidal and may destroy the bacterial host, such destruction does not occur until late in the fermentation cycle. Examples of regulated promoters are lambda $P_L$ and $P_R$, lac, gal, trp, ara, hut, and the like.

In a preferred embodiment, a genetic sequence coding for the cecropin-like polypeptide is operably linked to a genetic sequence coding for a polypeptide other than said cecropin-like polypeptide, such that the expression yields a fusion or precursor protein comprising both the amino acid sequence of the cecropin-like polypeptide, that of the additional residues and that of the additional polypeptide, and containing a selective cleavage site adjacent to the desired cecropin-like polypeptide amino acid sequence. The resulting fusion protein is not bactericidal. Bactericidally active cecropin-like polypeptide can then be isolated following selective cleavage.

Most commonly, cleavage will be effected outside the replicative environment of the expression vehicle, such as, for example, following harvest of the microbial culture. Thus, the additional polypeptide robs the cecropin-like polypeptide of its bactericidal effect pending extracellular cleavage, allowing the survival of the host for long enough time to yield high levels of the desired product. Preferably, the cecropin-like polypeptide will lack internal cleavage sites corresponding to the selective cleavage site employed to shed the superfluous polypeptide, although this is not necessarily an absolute condition. Since the cecropins are methionine free, cyanogen bromide cleavage at the methionine adjacent to the cecropin sequence is effective. The use of cyanogen bromide can simultaneously cleave the superfluous adjacent polypeptide and also transform the Met-X residues to a carboxy terminal homoserine.

The nature of the superfluous adjacent polypeptide comprising group X is not critical. It could either be part, whole or repetitive units of a known structural, enzymatic, hormonal, or other physiologically relevant protein. Alternatively, it could be a non-functional polypeptide. Without being bound by any particular theory, the inventors speculate that the increased length of the fusion protein somehow "masks" the bactericidal properties of the cecropin due to the varying conformation of the overall polypeptide. Preferably the genetic sequence coding for the adjacent superfluous polypeptide should be at least about greater than 300 base pairs in length, preferably between about 400 bp and 5 Kbp, most preferably between 400 bp and 2 Kbp. This corresponds to a superfluous polypeptide of preferably between about 100–1700 amino acid residues.

Any of a large number of superfluous polypeptides can be fused to the desired cecropin-like polypeptide sequence. The polypeptide gene sequence can either be prepared by organic synthesis, in which case optimization procedures would be recommended, or might be prepared by such techniques as reverse transcription of appropriate mRNA. Enzymatic coupling of the gene sequence for the polypeptide to the gene sequence for the structural cecropin peptide would then follow the preparation of the cDNA. Enzymatic coupling can be either by blunt ligation or by the provision of cohesive termini, comprising one of the two strands of a restriction endonuclease recognition site.

Examples of superfluous polypeptides are beta-galactosidase or ribulokinase (encoded for by the araB gene). Enzymes and structural proteins are preferred. Other products which can be used are products encoded by the following genes: aceA or aceB, araA, araB, araC, araD, argG, aroB, lacA, serA, purA, trpA, trpB, trpC, trpD, trpE, tyrA, and the like. The superfluous polypeptide is normally free of glycosylation. The araB promoter is the preferred promoter, although other promoters such as lambda $P_L$ and $P_R$, lac, gal, trp, hut, and other ara promoters may be used.

In yet another embodiment of the invention, the cecropin-like genetic sequence is operably linked to the sequence for a superfluous polypeptide capable, in the fusion product, of inhibiting or inactivating the bactericidal activity of the cecropin-like polypeptide and, in addition, to an inducible promoter. In this manner, both the effect obtainable through the fusion protein technique and the effect obtainable through the use of the inducible promoter can be exploited advantageously and simultaneously.

Although one embodiment of the present invention results in methods for producing cecropin-like polypeptides in cecropin-sensitive hosts, e.g., bacterial hosts, the genetic constructs prepared herein and the methods involved can also be utilized for expression of cecropin-like polypeptides in other, non-cecropin sensitive hosts. These cecropin insensitive hosts include yeasts, mammalian cell cultures and certain Gram-positive bacteria. Useful yeast and mammalian hosts and vectors are well known to those of skill in the art, and reference is made, for example, to European Patent Publication No. 0093619, published Nov. 9, 1983. Bacterial hosts can include those mentioned hereinabove with the araB promoter, as well as bacterial hosts such as the genera *Pseudomonas, Citrobacter, Xanthomonas,* and *Erwinia.* Any plasmid vector compatible with these hosts, as described above with the araB promoter, can be used.

Another preferred promoter for cecropin-like polypeptides is lambda ($P_L$). The genetic construct for the cecropin-like polypeptide and the superfluous polypeptide can be placed under the control of the leftward promoter of bacteriophage lambda ($P_L$). This promoter is one of the strongest known promoters which can be controlled. Control is exerted by the lambda repressor, and adjacent restriction sites are known. A temperature sensitive allele of the CI gene can be placed on the vector that contains the cecropin complete sequence or a different vector. When the temperature is raised to 42° C., the repressor is inactivated, and the promoter will be expressed at its maximum level. The amount of mRNA produced under these conditions should be sufficient to result in a cell which contains about 10% of its newly synthesized RNA originated from the $P_L$ promoter. In this scheme, it is possible to establish a bank of clones in which a functional cecropin-like polypeptide fusion construct sequence is placed adjacent to a ribosome binding sequence, and at varying distances from the lambda $P_L$ promoter. These clones can then be screened and the one giving the highest yield selected.

The expression of a cecropin-like polypeptide sequence can also be placed under control of other regulons which may be "homologous" to the organism in its untransformed state. For example, *E. coli* chromosomal DNA contains a lactose or lac operon which mediates lactose digestion by elaborating the enzyme beta-galactosidase. The lac control elements may be obtained from bacteriophage lambda plac5, which is infective for *E. coli.* The phage's lac operon can be derived by transduction from the same bacterial species. Regulons suitable for use in the process of the invention can be derived from plasmid DNA native to the organism. The lac promoter-operator system can be induced by IPTG.

Of particular interest in the present invention is to provide synthetic polynucleotide sequences coding for the cecropin-like polypeptides. In a preferred embodiment of the present invention, the synthetic sequence of the cecropin-like peptides (with adjacent sequences) is optimized so that expression thereof will be compatible with a variety of hosts such as yeasts and bacteria, especially the latter. In particular, optimization of the expression of any given sequence in *E. coli* is of great importance. Thus, after performing such optimization procedures as indicated above, the actual genetic sequence of the cecropin-like polypeptides with or without adjacent sequences, will usually be distinct from the naturally-occurring sequence in the original species.

In addition, the design of the desired gene for the fused product should preferably incorporate codons for amino acids at the cleavage site with the superfluous polypeptide such as methionine (cleavable by cyanogen bromide), tryptophan (clearable by o-iodosobenzoic acid), and the like. This said cleavage should result in the formation of a C-terminal residue which is capable of being modified by a variety of agents which will react specifically with the C-terminus. The use of methionine as the cleavage site (cleavable by cyanogen bromide) is preferred since the cleavage is very specific and results in a C-terminal homoserine lactone, which is readily modified.

In one embodiment of the invention, any given codon in the desired DNA sequence for the fusion product can be mutagenized at will through site-directed mutagenesis. Thus, it is possible, after synthesis of the desired DNA sequence, to introduce into the sequence a cleavable site. Site-directed mutagenesis is known, and reference is made to Wallace et al., Science 209:1396–1400 (1980), herein incorporated by reference.

Where the structural gene of the desired cecropin-like polypeptide is to be inserted into a vehicle for expression as such, the gene would be preceded by a "start" codon, and one or more termination or stop codons. When the expression product is a fusion protein comprising both the cecropin-like polypeptide and part or whole of an additional polypeptide, the start codon may be placed prior to the N-terminus of the superfluous polypeptide if it is leading.

Methods for the syntheses of polynucleotides are well known to one skilled in the art. Reference is made, for example, to the triester method of Ito et al., Nucl. Acid Res. 10:1755–1769 (1982).

The cecropin-like polypeptides produced by the methods of the invention can be used as broad antimicrobial agents directed toward specific applications. Such applications include but are not limited to, for example, the use of the cecropin-like polypeptides as preservatives in processed food targets (target organisms: *Salmonella, Yersinia, Shigella*); as a topical agent (target organisms: *Pseudomonas, Streptococcus*) or to kill odor producing microbes (target organism: *Micrococci*). The relative effectiveness of cecropin-like polypeptides for the applications described can be readily evaluated by one of skill in the art by determining sensitivity of any organism to one of the cecropin-like polypeptides. The same bacterial screen used in vitro can be utilized to determine dosages and concentrations.

Having now generally described this invention, the same will be better understood by reference to specific examples which are included herein for purposes of illustration only and are not intended to be limiting unless otherwise specified.

EXAMPLE I

Addition Of Met-Gly At The Carboxyl-Terminus By Primer-Directed Mutagenesis To Construct Plasmid PCAMG Plasmid pCAMG was constructed from plasmid pCA3D described in copending U.S. Pat. application Ser. No. 06/797,472 (now abandoned) which is incorporated herein by reference.

The primer directed mutagenesis technique of Miyada et al., Gene 17:167 (1982) was used to construct pCAMG, incorporated by reference herein.

Figure 2:
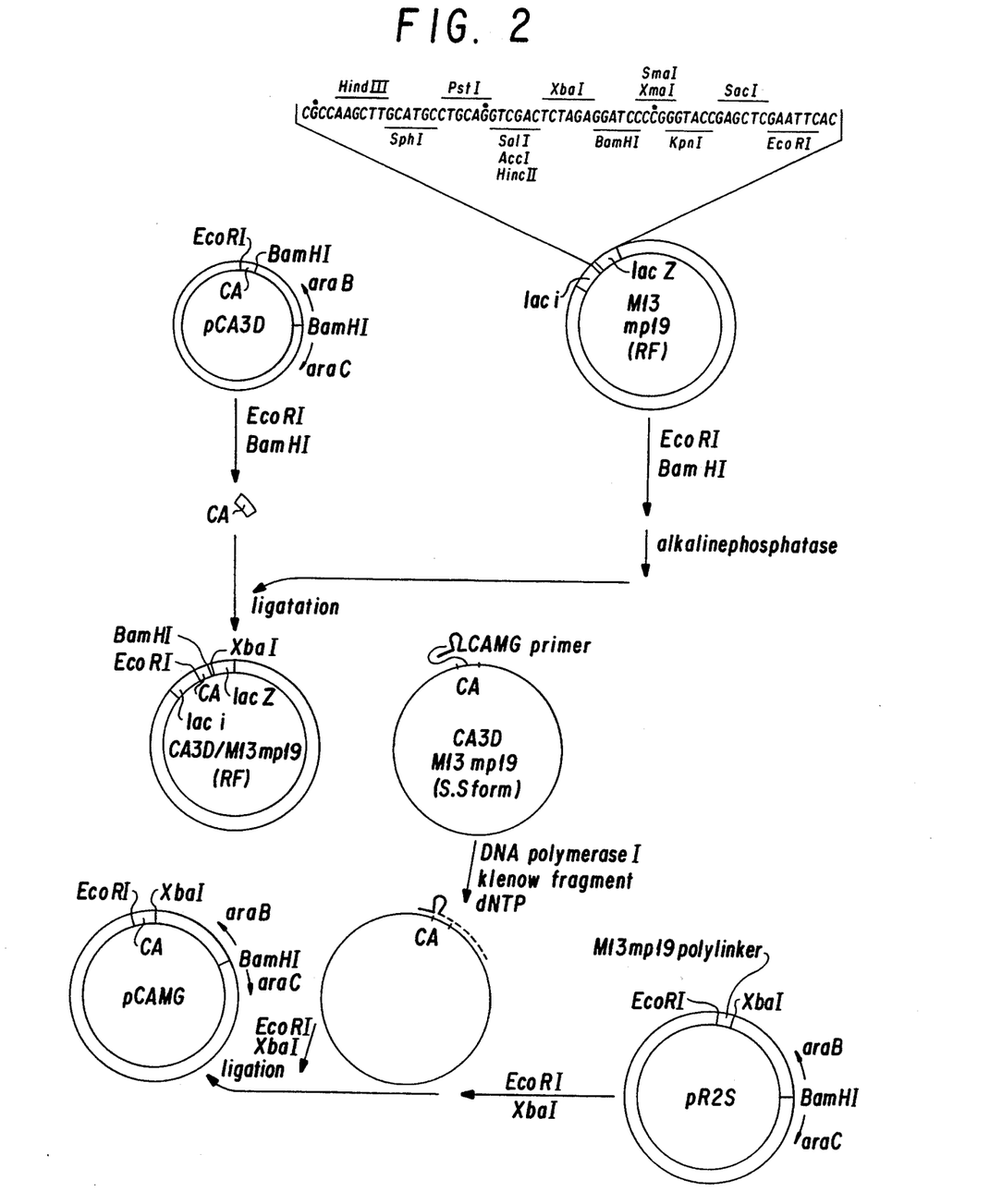
FIG. 2 shows the scheme for the construction of plasmid pCAMG.
Figure 3:
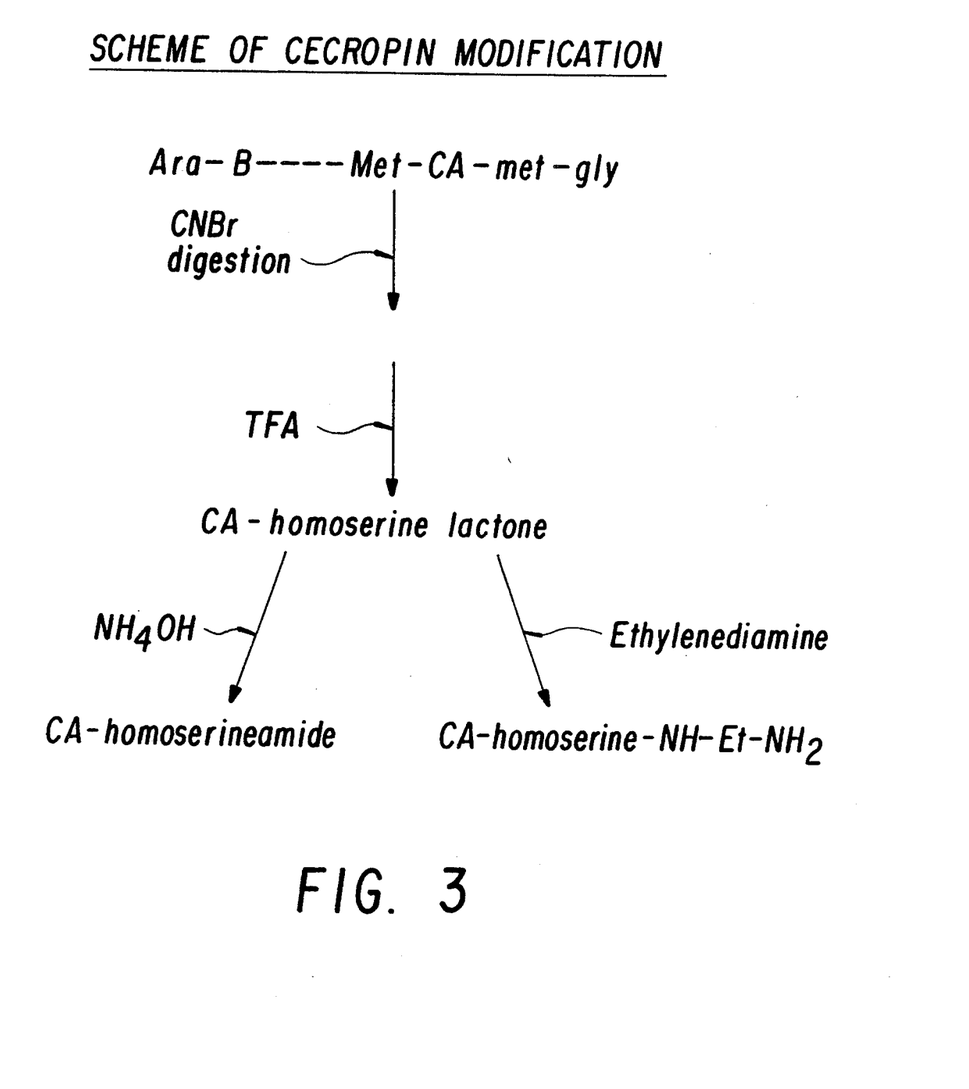
FIG. 3 shows the scheme for the production of genetically engineered cecropin with C-terminal modifications.

The mutagenesis scheme for changes at the carboxyl terminus of cecropin A is shown in FIG. 2.

Step I.

The EcoRI, BamHi cecropin A gene fragment was ligated into M13mp19 as follows: pCA3D was digested with restriction endonucleases BamHi and EcoRI to excise the cecropin A (CA) gene. This CA gene fragment was then ligated into the double-stranded replication form (RF) of M13mp19 which had been pre-treated with EcoRI, BamHI and alkaline phosphatase to obtain CA3D/M 13mp19.

Step II.

The CAMG primer (5'-AGTGAATTCTAT-TAACCCATT TFAGCG-3') for mutagenesis was annealed to single stranded M13mp19 as follows: One hundred ng of CAMG primer was mixed with 10 ug of the single-stranded form of CA3D/M 13mp19 in 50 ul of Hin buffer. The mixture was boiled at 100° C. for 3 rain in a beaker containing 800 ml of H$_2$O. The mixture was then allowed to cool slowly at room temperature to 37° C. to let the CAMG primer anneal to CA3D/M13mp19.

Step III.

Double-stranded DNA containing the mutagenized cecropin A gene was synthesized in vitro by extension of the primer for mutagenesis as follows: Primer extension was performed with DNA polymerase I Klenow fragment and dNTP at 37° C. for 2 hrs. The enzyme was inactivated by phenol extraction, and the DNA was recovered by ethanol precipitation.

Step IV.

Figure 1:
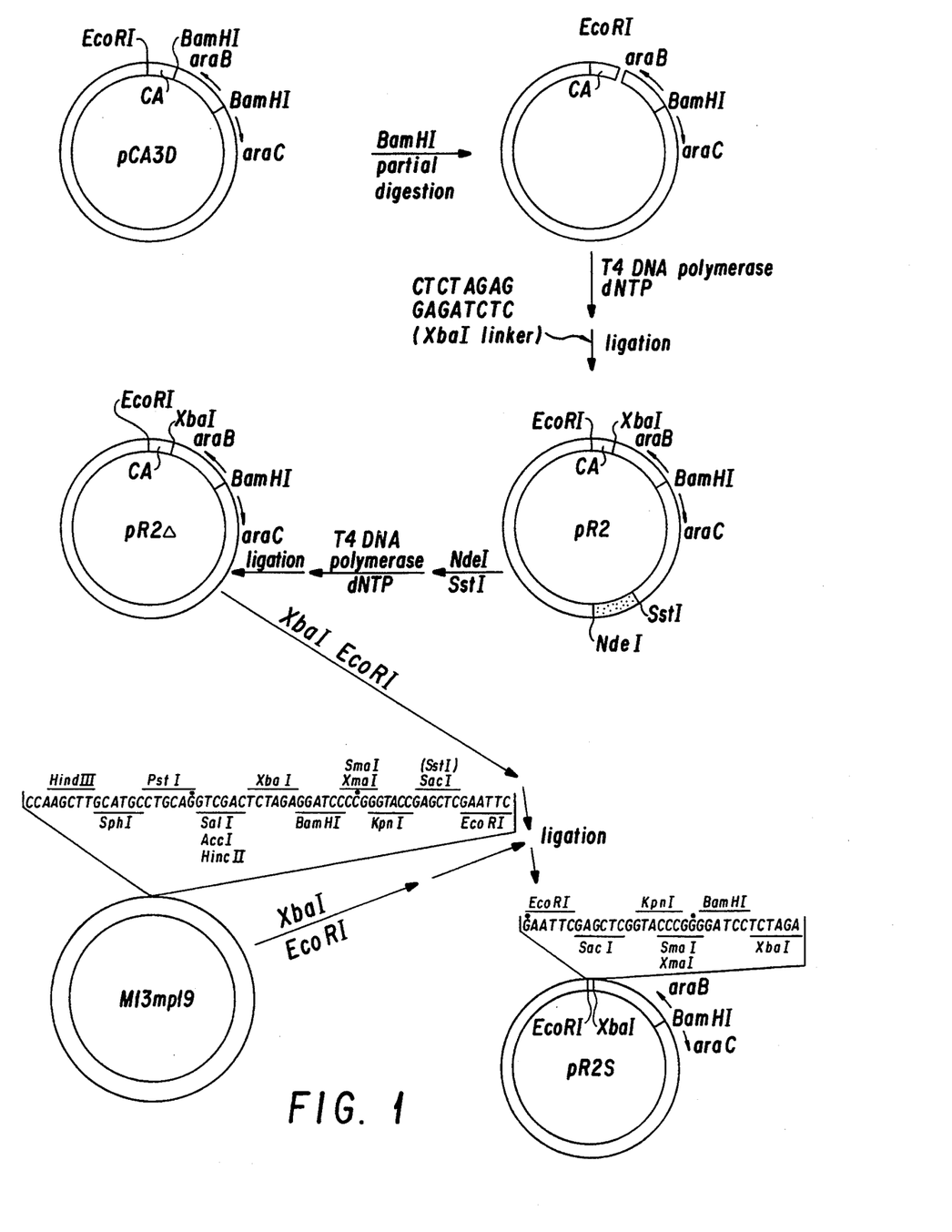
FIG. 1 shows a diagram for the construction of plasmid R2S.

The recipient plasmid pR2S was constructed as follows (FIG. 1): pCA3D was partially digested with BamHI, filled in with T4 DNA polymerase and then an XbaI linker CTCTAGAG was ligated just before the cecropin A gene to obtain pR2 which has a new XbaI site. pR2 was digested with NdeI and SstI, the sticky ends were bluntended with T4 DNA polymerase, and then ligated to obtain pR2 delta which lacks the SstI site. pR2 delta was digested with EcoRI and XbaI, then ligated with the EcoRI and XbaI digested RF form of M13mp19 to obtain pR2S. This vector contains araC, part of araB and a piece of M 13 that contains EcoRI, XbaI and other restriction enzyme sites (FIG. 1).

Step V.

The mutagenized cecropin A gene was cleaved from the M13 vector with EcoRI and XbaI and cloned into an unmutated recipient vector pR2S which had been pretreated with EcoRI and XbaI. The ligation mixture was digested with SstI to decrease the background of pR2S, then transformed into *E. coli* MC1061. Fifty potential clones were identified by colony hybridization using the CAMG primer as the probe. One of the clones that had the correct DNA sequence was called pCAMG.

EXAMPLE 2

Modifications of the C-terminus of Cecropin-Like Polypeptide A

Various C-terminal modifications were performed using a gene construct which codes for an additional methionyl-glycine at the C-terminus. FIGS. 1 and 2 depict the modification scheme used in the present invention.

A. C-Terminal Homoserine

An *E. coli* MC1061 strain containing the plasmid pCAMG was grown in a ten liter fermentation vessel to an O.D. at 600nm of 10, induced with 5 g/L of arabinose, grown for 7–10 hours, and then harvested. These cells were broken in a Gaulin homogenizer and the resulting solution was centrifuged at 14,000 xg for 30 minutes. The pellet from this centrifugation was then suspended in a 50 mM phosphate buffer containing 1 mM EDTA at a pH of 7–7.5 with the use of a blender and the suspension was centrifuged as before. The pellet was washed once more using this procedure and was then dissolved in 70% formic acid (1.6 liters per kg wet cell mass) to which 15 g of cyanogen bromide was added over a 6 hour period while the mixture was constantly stirred. This cyanogen bromide reaction was continued for 8–16 hours at room temperature after which the volume was reduced to 300 ml by the use of a rotary evaporator. The mixture was then treated with 10N NaOH to raise the pH to 3.5–4.0, then lyophilized.

The lyophilized powder was extracted with 1 liter of 1.7N sodium acetate [pH 4.0] with a conductivity of 15 mS. The material was mixed using a blender and the suspension was centrifuged as above. This extraction procedure is repeated 4–6 times and the supernatants were combined and diluted with an equal volume of deionized water, then applied to a Zetachrom SP-200 ion exchange disk and eluted with 500 mM $NH_4HCO_3$. The eluant was concentrated on an Amcicon TM YM-2 membrane. This material was then diluted with deionized water and concentrated twice more to reduce the $NH_4HCO_3$ concentration, then lyophilized and stored at $-20°$ C.

B. C-Terminal Homoserine Lactone

The lyophilized powder was then treated with concentrated trifluoroacetic acid (TFA) at 20–50 mg/ml of protein for one hour at room temperature. This converted the C-terminal homoserine into the lactone form (Horn, 1975; Kempe et al., 1985). The TFA treated material was solubilized in 0.05% TFA at approximately 2 mg/ml and was then injected on a semi-preparative C-18 reverse-phase HPLC column (20 mg per chromatogram) equilibrated with 0.05% TFA and eluted in a 37–42% acetonitrile gradient also containing 0.05% TFA.

C. C-Terminal Homoserine Amides

Formation of the homoserine amide was achieved by the treatment of the lactone with 30% $NH_4OH$ in a sealed ampule at 45° C. for 2.5 hours. The excess ammonia was removed by a nitrogen stream and the sample purified by reverse-phase HPLC using the conditions described above.

The addition of ethylenediamine to the carboxyl terminus was done using 5–20 ml of dimethylsulfoxide. Ethylenediamine was added to a concentration of 10 percent and the mixture was incubated at 37° C. with constant agitation (Horn, Analytical Biochem. 69:583–589 (1975)). Following the incubation period, 360 ul of trifluoroacetic acid was added and the sample was chromatographed on reverse-phase HPLC (as above). This enriched fraction was then chromatographed on an HPLC Mono S column (strong cation exchanger) equilibrated in 20 mM $NH_4HCO_3$ and eluted with an isocratic eluant of 220 mM $NH_4HCO_3$.

Figure 4:
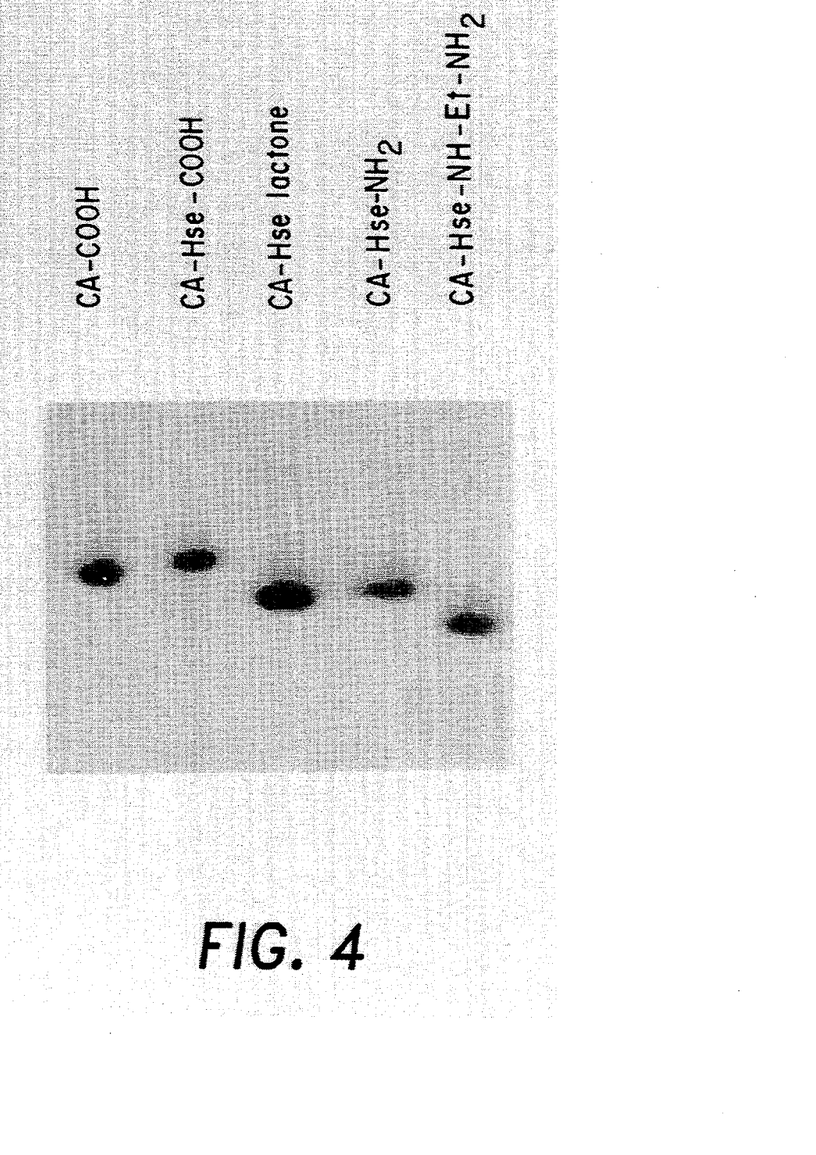
FIG. 4 shows a polyacylamide gel electrophoresis of the various forms of cecropin-like polypeptides.

The various forms of cecropin-like polypeptides generated by these procedures were subjected to polyacrylamide gel electrophoresis (FIG. 4) using a separating gel at pH 4.5 in the absence of ionic detergents (Reisfeld et al., Nature 195:281–283 (1962)). Any modification which changes the charge at the C-terminus can be distinguished by this technique. This gel also shows that each of the modified forms of cecropin-like polypeptide are highly enriched.

EXAMPLE 3

Assay of Bactericidal Activity

The assay for antimicrobial activity was performed by pouring 10 ml of agar in TYE media containing about $10^7$ viable cells of the test organisms. Wells, 2 mm in diameter, were punched in the agar plates. Aliquots of the modified cecropin-like polypeptides (2–12 ul) were then added to each well. The diameter of the inhibition zones, or haloes, around the wells, were measured after overnight incubation at 25° C.

The activities of various cecropin-like polypeptides were tested against both Gram-negative and Gram-positive organisms. Anti-microbial activity against the Gram-negative organisms remained unaltered for most of the Gram-negative bacteria (except, i.e., *Serratia marcescens*) as shown in Table 1. Only those peptides modified at the C-terminal carboxyl group were found to have significant activity against Gram-positive bacteria (See Table 2). To determine a standard of halo formation, the various modified cecropin-like polypeptides were also applied to *E. coli* D21. Activity shown in Tables 1 and 2 is expressed as the ratio of the radius of the cleared halo for each organism versus that for *E. coli* D21.

The cecropin-like polypeptide modified at the carboxy terminus with ehtylenediamine and naturally occurring cecropin A were tested against a variety of organisms. The relative activities of the antimicrobial agents were expressed per nanomole of polypeptide applied to each well (Table 3). The data shows that the modified material is more potent per nanomole than naturally occurring cecropin against a broad range of organisms.

Although the foregoing invention has been described in some detail by way of illustration and example for purposes of clarity of understanding, it will be obvious that certain changes and modifications may be practiced within the scope of the invention, as limited by the scope of the appended claims.

TABLE 1

| RELATIVE ACTIVITY OF MODIFIED CECROPINS AGAINST GRAM-NEGATIVE BACTERIA[a] | | | | |
|---|---|---|---|---|
| MODIFIED[b] CECROPINS | *E. coli*[c] | *S. typhimurium* | *E. cloacae* | *P. aeruginosa* |
| CA—COOH | 0.84 | 1.09 | 0.84 | 0.70 |
| CA—HS—COOH | 0.86 | 1.07 | 0.79 | 0.76 |
| CA—HS—LACTONE | 0.84 | 1.03 | 0.88 | 0.80 |
| CA—HS—$NH_2$ | 0.81 | 1.09 | 0.86 | 0.71 |
| CA—$NH_2$[d] | 0.80 | 1.06 | 0.92 | 0.70 |

[a]Activity is expressed as the ratio of the radius of the cleared halo for each organism versus that for *E. coli* D21.
[b]Refers to chemically modified C-termini of genetically engineered cecropin A.
[c]MC1061
[d]CA—$NH_2$ is cecropin A as isolated from *cecropia* pupae.

TABLE 2

| RELATIVE ACTIVITY OF MODIFIED CECROPINS AGAINST GRAM-POSITIVE BACTERIA[a] | | | | |
|---|---|---|---|---|
| MODIFIED[b] CECROPINS | *M. luteus* | *B. megaterium* | *B. subtilis* | *S. faecalis* |
| CA—COOH | 0 | 0.2 ± 0.08 | 0 | 0 |
| CA—HS—COOH | 0.1 ± 0.1 | 0.5 ± 0.1 | 0 | 0 |
| CA—HS—LACTONE | 1.2 ± 0.1 | 0.8 ± 0.1 | 0.3 ± 0.1 | 0.1 ± 0.03 |

TABLE 2-continued

RELATIVE ACTIVITY OF MODIFIED CECROPINS AGAINST GRAM-POSITIVE BACTERIA[a]

| MODIFIED[b] CECROPINS | M. luteus | B. megaterium | B. subtilis | S. faecalis |
|---|---|---|---|---|
| CA—HS—NH$_2$ | 1.4 ± 0.2 | 0.4 ± 0.2 | 0.06 ± 0.06 | 0 |
| CA—HS—NH—Et—NH$_2$ | 1.2 ± 0.05 | 0.7 ± 0.05 | 0.4 ± 0.1 | 0.35 ± 0.1 |
| CA—NH$_2$[c] | 1.2 ± 0.2 | 0.7 ± 0.05 | 0.1 ± 0.05 | 0 |

[a]Activity is expressed as the ratio of the radius of the cleared halo for each organism versus that for E. coli D21
[b]Refers to chemically modified C-termini of genetically engineered cecropin A.
[c]CA—NH$_2$ is cecropin A as isolated from *cecropia* pupae.

TABLE 3

COMPARISON OF CECROPIN A TO THE MODIFIED CECROPIN CA—HS—NH—Et—NH

| Microorganism | Activity[a] per Nanomole[b] | |
|---|---|---|
| | Cecropin A | CA—HS—NH—Et—NH$_2$ |
| *Escherichia coli* | 6.1 | 9.8 |
| *Micrococcus luteus* | 6.1 | 12.0 |
| *Bacillus megaterium* | 5.1 | 6.9 |
| *Bacillus subtilus* | <0.5 | 2.7 |
| *Streptococcus faecalis* | <0.5 | 1.2 |

[a]Activity measured by halo assay, represents the radius of the inhibitory ring in millimeters.
[b]Nanomoles determined by amino acid analysis.

What is claimed is:

1. A recombinant DNA molecule comprising a genetic sequence coding for a cecropin polypeptide which is extended at the C-terminus thereof by Met-X wherein X is a group which is clearable from methionine by CNBr.

2. The recombinant DNA molecule of claim 1, wherein X is an amine acid or peptide residue.

3. The recombinant DNA molecule of claim 1, wherein said cecropin polypeptide is homologous to cecropin A.

4. The recombinant DNA molecule of claim 2, wherein said cecropin polypeptide is homologous to cecropin A.

5. An expression vehicle replicable in a given host comprising the recombinant DNA molecule of any of claims 1-4.

6. The expression vehicle of claim 5, which is a plasmid.

7. The expression vehicle of claim 5, wherein said host is a bacterium.

8. A method of producing a cecropin polypeptide which is extended by a homoserine residue at the C-terminus thereof which comprises:
    transforming a suitable host with the expression vehicle of claim 5;
    culturing said host;
    recovering said cecropin polypeptide, having a Met-X at the C-terminus thereof; and
    cleaving said Met-X to thereby produce a C-terminal homoserine.

9. A pharmaceutical composition with antimicrobial activity, comprising an effective amount of a cecropin polypeptide which is extended by a homoserine residue at the C-terminus thereof.

* * * * *

UNITED STATES PATENT AND TRADEMARK OFFICE
CERTIFICATE OF CORRECTION

PATENT NO. : 5,344,765
DATED : September 6, 1994
INVENTOR(S) : Lai et al.

It is certified that error appears in the above-indentified patent and that said Letters Patent is hereby corrected as shown below:

Column 13, claim 1, line 30, change "clearable" to --cleavable--.
Column 13, claim 2, line 33, change "amine" to --amino--.

Signed and Sealed this

Twenty-ninth Day of November, 1994

Attest:

BRUCE LEHMAN

*Attesting Officer*     *Commissioner of Patents and Trademarks*